United States Patent
Porras et al.

(10) Patent No.: US 6,193,976 B1
(45) Date of Patent: Feb. 27, 2001

(54) HAIR RESTORER CONTAINING VETIVER GRASS EXTRACT

(75) Inventors: Sandra E. Porras, San Diego, CA (US); Francisco Grippa Jochamowitz, Iquitos (PE)

(73) Assignee: Nupel, Inc., San Diego, CA (US)

( * ) Notice: Subject to any disclaimer, the term of this patent is extended or adjusted under 35 U.S.C. 154(b) by 0 days.

(21) Appl. No.: 09/318,665

(22) Filed: May 25, 1999

(51) Int. Cl.[7] ............................... A61K 35/78; A61K 7/06
(52) U.S. Cl. ........................ 424/195.1; 424/70.1; 424/74; 514/880
(58) Field of Search ............................... 424/195.1, 70.1, 424/74; 514/880

(56) References Cited

U.S. PATENT DOCUMENTS

| | | | |
|---|---|---|---|
| 5,246,693 | * 9/1993 | Grollier et al. | 424/70 |
| 5,494,667 | 2/1996 | Uchida et al. | |
| 5,597,575 | 1/1997 | Breithbarth . | |
| 5,665,342 | 9/1997 | Salinas . | |
| 5,674,510 | 10/1997 | DiTucci . | |
| 5,679,378 | 10/1997 | Fischer . | |
| 5,695,748 | 12/1997 | Francis . | |
| 5,744,128 | 4/1998 | Holick . | |
| 5,750,108 | 5/1998 | Edwards . | |

FOREIGN PATENT DOCUMENTS

07061918 * 3/1995 (JP) .

OTHER PUBLICATIONS

Grimshaw, R.G., The Role of Vetiver Grass in Sustaining Agricultural Productivity, 10 pp. date not disclosed.

Brunner, D.R., Specimen Data: Vetiveria zizanioides (L.) Nash, 1985.

Zardini E., & C. Cuevas, Specimen Data: Vetiveria zizanioides (L.) Nash, 1988.

W.H. Lewis, et al. (I), Specimen Data: Vetiveria zizanioides (L.) Nash, 1986.

W.H. Lewis, et al. (II), Specimen Data: Vetiveria zizanioides (L.) Nash, 1987.

J.A. Orihuela, Vetiver Grass in Peru, May 21, 1986, 2 pages.

Raven et al. *Biology of Plants* 3d.ed., (1981) Chapt. 10, pp169–183.

* cited by examiner

*Primary Examiner*—Christopher Tate
(74) *Attorney, Agent, or Firm*—Knobbe Martens Olson & bear, LLP

(57) ABSTRACT

The present invention includes methods for the treatment and/or prevention of hair loss and methods for the regeneration or restoration of hair growth comprising a step of identifying an individual suffering from or susceptible to hair loss or hair thinning or in need of hair regeneration, and a step of administering an extract of the root of a Vetiver grass. Preferably, the extract is an aqueous extract and is administered topically. Also preferably, the Vetiver grass is a subspecies of *Vetiveria zizanioides*, and is most preferably *Vetiveria zizanioides* (L.) Nash. The present invention also provides a composition, preferably in the from of a lotion, gel, cream, or other suspension, and a distinct chemical compound or class of chemical compounds therein, effective in restoring hair growth, preventing hair loss, and/or reversing the effects of hair thinning. The composition may include an effective amount of a hair loss preventative or hair growth promoting composition isolatable as an extract of the roots of a Vetiver grass, together with a pharmaceutically-acceptable topical carrier other than water.

20 Claims, No Drawings

HAIR RESTORER CONTAINING VETIVER GRASS EXTRACT

BACKGROUND OF THE INVENTION

1. Field of the Invention

The present invention relates to a composition containing an extract of Vetiver grass, having the effect of increasing or restoring hair growth, and/or preventing hair loss. More specifically, the present invention relates to a hair growth restoring and/or hair loss preventing composition containing an extract of the root of the plant *Vetiveria zizanioides*.

2. Description of the Related Art

Efforts to Restore Hair Growth and/or Prevent Hair Loss

The recorded literature, including the medical, scientific and patent literature, relates various efforts to treat and/or prevent hair loss and to restore and/or encourage hair growth, particularly regarding hair on the human scalp. Some of these efforts have met with varying degrees of success, ranging from complete failure to more-recently available topically administered drugs such as Rogaine® (active ingredient, minoxidil) and orally administered drugs such as Propecia® (active ingredient, finasteride). The active ingredients in these two drugs have been approved by the United States Food and Drug Administration for promoting hair growth. Rogaine® and Propecia® exhibit some degree of success in promoting and/or restoring hair growth, particularly hair loss at the vertex or crown of the head, but administration of these drugs may lead to certain adverse side effects, including for example sexual dysfunction. Moreover, Rogaine® and Propecia® are to be used on a continual basis and are relatively expensive. Accordingly, individuals with thinning hair or hair loss, or individuals likely to experience thinning hair or hair loss, especially men with thinning hair or hair loss on the scalp or, more particularly, on the vertex of the head, are in need of alternative treatments to encourage and/or restore hair growth.

Accordingly, there have been a variety of efforts to fulfill this need. As evidence of these efforts, the PTO has granted approximately 100 patents on methods and or compositions for treating hair loss and/or thinning hair. Among these patent are patents that disclose baldness remedies made from botanical, vegetative, or other found materials. For example, these patents include U.S. Pat. No. 5,679,378 (for the topical use of dead sea mud); U.S. Pat. No. 5,744,128 (for the topical use of emu oil); U.S. Pat. No. 5,665,342 (for the topical use of potato peelings and lantana leaves); U.S. Pat. No. 5,597,575 (for the topical use of vitamin D3 and aloe); U.S. Pat. No. 5,674,510 (for the topical use of garlic powder, brewers yeast, grapefruit, acidic acid and kelp); U.S. Pat. No. 5,750,108 (for the topical use of tea tree oil, chlorine dioxide and acidic solution and saw palmetto berry extract); U.S. Pat. No. 5,695,748 (for the topical use of sage, aloe and nettles, castor oil, shea butter, wheat germ oil and white iodine) and U.S. Pat. No. 5,494,667 (for the topical use of pine extract and bamboo extract or Japanese apricot). The United States Food and Drug Administration had not determined whether these methods and/or compositions of treating hair loss and restoring hair growth are uniformly safe and effective.

Vetiver Grass

There are at least seventeen known varieties of Vetiver grass, the most common of which is *Vetiveria zizanioides*. The taxonomic information of the Vetiver grasses, which are often also generically referred to as Vetiveria Bory, is as follows: Family-Graminae (Poaceae); Subfamily-Panicoideae; Tribe-Andropogoneae; subtribe-Sorghinae. Vetiver grasses are common to flood plains and stream banks and are generically described as follows: They are tufted perennials, having a line of hairs at the ligule; the inflorescence is a panicle. The primary branches of the panicle are whorled, simple, and each bears a raceme. The raceme is typically long and slender, comprising (20)3–10 spikelet pairs. The spikelet are sessile and laterally compressed, and the plant's callus is obtuse to pungent, and is often large and concical. The lower glume is chartaceous to coriaceous, spinulose, and the upper glume is shortly awned. See, e.g., Watson, L. and M. J. Dallwitz (1989) *Grass Genera of the World*, Australian National University Printing Service, Canberra. Further information regarding the Vetiver grasses may be obtained from The Vetiver Network at 15 Wirt Street NW, Leesburg Va. 20176 USA, phone: (703) 771-1942, facsimile: (703) 771-8260 (Email: vetiver@vetiver.org; Home page: http://www.vetiver.org/).

Specimens of the *Vetiveria zizanioides* (L.) Nash subspecies of Vetriver grass have been identified in Paraguay (in the State of Paraguari) by David R. Brenner at 250 m, 25.54 S 54.09 W and by Elissa Zardini and C. Cuevas at 500 m, 25.54 S 54.09 W, and in Peru (in the State of Loreto) by W. H. Lewis, M. Elvin-Lewis, M. C. Gnerre, and C. Diaz at 160 m, 3.15 S 25.50 W. According to the reports of W. H. Lewis et al., the native people in the State of Loreto in Peru, who identify the *Vetiveria zizanioides* (L.) Nash subspecies by the name "pachuli," crush the root and rhizome, and use the obtained juice to wash their hair. These native people are also reported to have boiled the root, and used the decoction to wash their hair. In other acounts, the roots of this plant have also been reported to have been used by the native people of Loreto as a medicine to treat, among other conditions, dermatitis, hemorrhoids, fever, rheumatism, and neuralgia, and have been used for the control of fungal growth. However, use to prevent hair loss or to facilitate hair growth is not known.

SUMMARY OF THE INVENTION

The present invention includes methods for the treatment and/or prevention of hair loss and methods for the regeneration or restoration of hair growth comprising a step of identifying an individual suffering from or susceptible to hair loss or hair thinning or in need of hair regeneration, and a step of administering an extract of the root of a Vetiver grass. Preferably, the extract is an aqueous extract and is administered topically. Also preferably, the Vetiver grass is a subspecies of *Vetiveria zizanioides*, and is most preferably *Vetiveria zizanioides* (L.) Nash. The present invention also provides a composition, preferably in the from of a lotion, gel, cream, or other suspension, and a distinct chemical compound or class of chemical compounds therein, effective in restoring hair growth, preventing hair loss, and/or reversing the effects of hair thinning. The composition may include an effective amount of a hair loss preventative or hair growth promoting composition isolatable as an extract of the roots of a Vetiver grass, together with a pharmaceutically-acceptable topical carrier other than water.

DETAILED DESCRIPTION OF THE PREFERRED EMBODIMENT

One object of the present invention is to provide a non-toxic hair growth restorer and/or hair loss preventer. Another object of the present invention is to provide a relatively inexpensive hair growth restoring composition or hair loss preventing composition, including a compound or class of compounds having the effect of restoring hair growth and/or preventing hair loss. Another objective of the present invention is to provide an ingestable, injectable, or topically-applicable composition for restoring hair growth and/or preventing hair loss. Yet another object of the present invention is to provide a renewable resource for a hair growth restorer or hair loss preventing compound or class of compounds. It shall be understood that the invention as described and claimed herein should optimally satisfy more than one of the objects of the present invention, but need not simultaneously satisfy all, or even one, of the objects of the present invention, nor need it satisfy any particular object of the invention.

As used herein, the terms "restore hair growth," "hair restorer," and "to restore hair growth" are essentially interchangeable. Each refers to methods or compositions for increasing the amount of hair growth. These phrases do not necessarily refer to the production of a full head of hair, nor do they refer to the restoration of hair growth to the state before the onset of hair loss or hair thinning. More precisely, these phrases and specifically the phrase "restore hair growth" should be interpreted consistently with their uses in U.S. Pat. Nos. 5,695,748, 5,679,378, and 5,578,599, the disclosures of which are incorporated by reference herein. Most typically, although not exclusively, "restore hair growth" refers to increasing the amount of hair growth at the vertex or crown of the head or at the front of the hair near the hair line, and most typically, although not exclusively, refers to human males.

As used herein, the terms "prevent hair loss," "hair loss preventer," and "to prevent hair loss" are essentially interchangeable. Each refers to methods or compositions for preventing the degree of hair loss. "Hair loss," as that term is used herein, includes hair thinning. These phrases do not necessarily refer to the complete cessation of hair loss or of hair thinning; rather, they refer to any measurable slowing in the rate of hair loss, as measured by standard measurements such as follicle count per unit skin area or by mass of hair per unit skin area. Such hair loss may be brought on by any of a variety of conditions, as will be understood by those of skill in the art. These phrases should not be interpreted inconsistently with the phrase "restore hair growth", as used in U.S. Pat. No. 5,695,748, 5,679,378, and 5,578,599. Most typically, although not exclusively, "prevent hair loss" refers to preventing the amount of hair lost at the vertex or crown of the head or at the front of the hair near the hair line, and most typically, although not exclusively, refers to human males.

As used herein, the phrases "hair loss" and "thinning hair," both refer to the state in which fewer hair follicles per unit area (hair count) on the skin are produced than in a state prior to the onset of hair loss or hair thinning, and may also refer to the state in which less mass of hair per unit skin area is produced than in a state prior to the onset of hair loss or hair thinning. Most typically, although not exclusively, "hair loss" refers to the amount of hair at the vertex or crown of the head or at the front of the hair near the hair line, and most typically, although not exclusively, refers to human males.

As used herein, the generic terms "Vetiver grass" or "Vetiver grasses" or "Vetiveria Bory" refer to the plants known and referred to as members of the Family Graminae (Poaceae), the Subfamily Panicoideae, the Tribe Andropogoneae; and the Subtribe Sorghinae. Specific, currently-known examples of Vetiver grasses include the *Vetiveria zizanioides* subspecies, *Vetiveria zizaniodides* (L.) Nash, Small, Fl. Southeast U.S. 67, 1326 (1903), and *Vetiveria zizaniodides* (L.) Nash var. tonkinensis, A. Camus, Bull. Mus. Nat. Hist. 25:674 (1919). Vetiver grasses also include the following species: *Vetiveria arguta*, (Steud.) C. E. Hubb., Kew Bull. Misc. Inf. 1939:654 (1939); *Vetiveria elongata*, (R.Br.) Stapf, Kew Bull. Misc. Inf. 1934:44 (1944); *Vetiveria filipes*, (Benth.) C. E. Hubb., Kew Bull. Misc. Inf. 1394L44 (1944); *Vetiveria filipes*, (Benth.) C. E. Hubb. var. *arundinacea* (Reeder) Jansen, Acta Bot. Neerl. 2:286 (1953); *Vetiveria fulvibarbis*, (Trin.) Stapf, Fl. Trop. Afr. 9:158 (1917); *Vetiveria intermedia*, S. T. Blake, Queensl. Univ. Dept. Biol. Papers 2(3):21 (1944); *Vetiveria lawsoni*, (Hook.f.) Blatter & McCann, Journ. Bombay Not.Hist.Soc. 32:409 (1928); *Vetiveria nigritana*, (Benth.) Stapf, Fl. Trop. Afr. 9:157 (1917); *Vetiveria pauciflora*, S. T. Blake, Queensl. Univ. Dept. Biol. Papers 2(3):20 (1944); *Vetiveria rigida*, B. K. Simon, Austrobaileya 3(1):95 (1989), and may also include: *Vetiveria arundinacea, Vitiveria festucoides, Vetiveria muricata, Vetiveria odorata*, and *Vetiveria odovatissima* Bory. Furthermore, the Vetiver grasses may include *Vetiveria venustus* and *Vetiveria nemoralis*, but these species are also typically categorized as, respectively, *Hemisorghum venustus* and *Chrysopogen nemoralis*.

The most common of the known varieties of Vetiver grass is *Vetiveria zizanioides*. Among the known subspecies of Vetiveria zizanioides is the subspecies Vetiveria zizanioides (L.) Nash. A specimen of this subspecies has been identified in Paraguay (in the State of Paraguari) by David R. Brenner at 250 m, 25.54 S 54.09 W and by Elissa Zardini and C. Cuevas at 500 m, 25.54 S 54.09 W. Furthermore, a specimen of this subspecies has been identified in Peru (in the State of Loreto) by W. H. Lewis, M. Elvin-Lewis, M. C. Gnerre, and C. Diaz at 160 m, 3.15 S 25.50 W.

*Vetiveria zizanioides* (L.) Nash is described as follows: It is a densely tufted, awnless, wiry, glabrous perennial grass. The plant grows in large clumps from a much-branched root stock with erect culms 0.5–1.5 meters high. The leaf blades are relatively stiff, long and narrow, usually up to 75 centimeters long and 8 millimeters or less in width, and glabrous but "downward rough" along the edges. The panicles are typically 15–30 centimeters long, and are narrow, acute, appressed, awnless, with one sessile spikelet; they are hermaphroditic, somewhat flattened laterally, and typically have short sharp spines, three stamens, and two plumose stigmas; the other spikelets are pedicelled and staminate. Some cultivated forms seldom flower. Furthermore, the leaves are basal and cauline. The blades are elongate, to 0.8 meters long, thick, and usually conduplicate basally, splitting along midrib apically, pubescent basally. They are sometimes purple, margins revolute, uppermost usually with vitreous spines; sheaths glabrous; ligule a fringe of hairs, 0.3–1.0 millimeters long. Inflorescence of spike-like branches; spike-like branches numerous, racemose, usually purple; rachis disarticulating at base of sessile spikelet. Spikelets paired (1 sessile and perfect, the other pedicellate and neuter or staminate), dorsally compressed, 2-floreted (upper floret perfect or staminate, lower floret neuter or staminate). Sessile spikelet is about 5 mm long; glumes acuminate, coriaceous, nerveless, about 5 mm long, vitreous, papillose spinose; lemmas acuminate, purple tinged, apex scarious, margins scarious, inrolled, softly ciliate, about 3.5 mm long; paleas scarious, about 2 mm long, margins inrolled, caryopsis not seen. Pedicellate spikelet slightly smaller than sessile spikelet. See, e.g., World Bank Handbook (1993); *Vetiver Grass-A Method of Vegetative Soil and Moisture Conservation*, Allen, Charles M. (1980).

*Vetiveria zizanioides* (L.) Nash may be indexed in herbaria under the following synonyms: *Andropogon zizanio-*

*ides* Linn.; *Andropogon squarrosus* Hack; *Andropogon muricatus* Retz.; *Andropogon nardus* Blanco; *Andropogon nigritanus* Stapf.; *Andropogon festucoides* Presl.; *Andropogon echinulatum* Koenig; *Anatherum zizanioides* Linn.; *Anatherum muricatum* Beauv.; *Agrostis verticillata* Lam; *Phalaris zizanioides* Linn.

As used herein, "roof" refers to all portions of the subterranean portion of a specifically or generically identified plant, including, but not limited to, the roots, the rhizomes, and the stolons of the identified plant.

As used herein, "individual" refers to any mammal that in a state unaffected by hair loss, will tend to grow hair. The preferred individual for use of the treatment and method of the present invention is a human, and a most preferred individual is a human male afflicted with adult-onset male pattern baldness. The Stumptail Macaque monkey, a species that exhibits a pathogenesis of balding similar to that of humans, are another preferred individual. It will be understood by those of skill in the art that the Stumptail Macaque monkey may be the subject of non-human clinical trials of the compositions and methods of the present invention.

As used herein, the term "water" refers to water, preferably potable water, more preferably spring water, and most preferably purified water, that is not diluted with a significant amount of alcohol or other water-miscible solvent, and does not have dissolved within it a significant amount of a water-soluble solute.

As used herein, the term "isolated" refers to the compound of class of compounds of the present invention being free of other, dissimilar compounds with which the compound of the invention is normally associated in its natural state, so that the compound of the invention comprises at least 0.5%, 1%, 5%, 10%, or 20%, and most preferably at least 50% of the mass, by weight, of a given sample. Such a sample may be used in the methods of the present invention directed, or may added to particular carriers or diluents as the composition of the present invention or when used in the methods of the present invention. As used herein, the term "isolatable" means capable of being isolated.

Preferred methods of the present invention generally include a first step of identifying an individual suffering from hair loss or hair thinning, or likely to experience hair loss or hair thinning. One such condition, which may be linked to a genetic marker, is known as *androgenetic alopecia*. Identification of such a condition, or the likelihood of experiencing such a condition, may be made by direct observation, as appreciated by those of skill in the art, or by evaluation of the phenotype of an individual's genetic relatives. As will be understood by those of skill in the art, an individual's likelihood of experiencing hair loss generally increases as that individual's genetic relatives, most typically the male, maternal genetic relatives of the individual, are identified as having experienced hair loss or hair thinning or, more specifically, *androgenetic alopecia*. This observation is especially true of human males and male Stumptail Macaque monkey, a species that exhibits a pathogenesis of balding similar to that of humans, having genetic male relatives who have experienced hair loss or hair thinning, especially adult-onset male pattern baldness. However, it is also true with respect to other individuals and to human females having genetic relatives who have experienced hair loss or hair thinning. Furthermore, genetic markers are identifiable for identifying individuals likely to experience hair loss of hair thinning; these markers may be used to identify an individual or the individual's genetic relatives consistent with the first step of the preferred methods of the present invention. Most preferably, an individual is identified by direct observation of hair loss or hair thinning over time. Such direct observation may be by the individual, a member of the individual's family, or by another, including but not limited to hair-care or medical professionals.

Preferred methods of the present invention generally include a subsequent step of applying or administering a composition comprising an extract of the root of a Vetiver grass. This extract may be either an aqueous extract, an alcoholic extract, or an organic extract. Most preferably, the extract is an aqueous extract. More specifically, the Vetiver grass root may be extracted from an hydroxylic solvent (e.g., water, $C_1$–$C_8$ alcohols, preferably methanol, ethanol, isopropanol), from a polar aprotic solvent (e.g., acetonitrile, dimethylformamide (DMF), dimethyl sulfoxide, acetone), or from a relatively non-polar organic solvent (e.g., benzene, toluene, liquid alkanes, preferably $C_4$–$C_8$ alkanes), or any suitable combination thereof. Salts, detergents, and other additives may be added to these solvents to facilitate extraction as will be appreciated by those of skill in the art.

The roots may be extracted, for example, within approximately the following weight to volume ratios to solvent: from 1 gram root: 1 liter solvent to 100 gram root: 1 milliliters solvent, and most preferably 1 gram root: 1 milliliter solvent. The duration of extraction may be as short a duration as one minute, ten minutes, an hour, overnight, a full day, a week, and for as long a duration as one month, depending on the solvent selected and the condition of the root. Furthermore, the solvent/root mixture may be left at room temperature cooled to any temperature above the freezing point of the solvent (e.g., 5° C., 10° C., or 20° C., where the solvent is water), and heated (e.g., approximately 50° C., 60° C., 70° C., 80, 90, or 95° C., where the solvent is water), or even heated to a boil. If the solvent is boiled, which is not typically preferred, it is preferred that the vapors be refluxed to preserve the active compound or class of compounds of the extract. Also, the root may be left whole, chopped, pureed, blended, or partly chopped, pureed, or blended prior to or upon addition to the solvent. Also, the Vetriver grass rhizomes, stolons, or roots may be separated and separately left whole, chopped, pureed, or blended and then extracted to yield the compounds or classes of compounds of the invention. As will be appreciated by those of skill in the art, repeated, sequential extractions in a single or a variety of different solvents may be performed. Suitable non-toxic solvents may be selected for the final extraction, if a series of extractions is performed.

Of the hydroxylic solvents, water is most preferred as a solvent. The $C_1$–$C_8$ alcohols are also preferred; most preferably among the alcohols are ethanol, methanol, isopropanol, and butanol. Of the polar aprotic solvents, DMF and acetone are most preferred. Of the organic solvents, benzene and toluene are most preferred.

The extract of the root of the Vetiver grass may be of any of the Vetiver grasses herein described, either generically or specifically. A preferred species of Vetiver grass is Vetiveria zizanioides, including the *Vetiveria zizanioides* (L.) Nash sub-species.

The preferred hair loss preventing and/or hair growth restoring composition of the present invention is a simple aqueous extract of the root of the *Vetiveria zizanioides* plant. In other embodiments, this composition may include, but need not necessarily include, pharmaceutically acceptable carriers that will allow the composition to be prepared for storage and subsequent administration. Such compositions, nonetheless, should contain a pharmaceutically effective amount of the compounds or class of compounds of the present invention, in a pharmaceutically acceptable carrier or diluent. Such acceptable carriers or diluents are described, for example, in Remington's Pharmaceutical Sciences, Mack Publishing Co. (A. R. Gennaro edit. 1985). Preservatives, stabilizers, dyes, flavoring agents (especially where the composition is administered orally) or aromatic agents (especially where the composition is topically applied) may be provided in the pharmaceutical composition. Also, sodium benzoate, sorbic acid and p-hydroxybenzoic acid esters, antioxidants, and/or suspending agents may be added as preservatives.

The preferred compound of class of compounds effective in preventing hair loss and/or restoring hair growth may be identified and isolated from the root of a Vetiver grass by standard analytical chemical methods. These methods include, but are not limited to column elution or column electrophoresis followed by fractionation and chemical and/or pharmacological analysis of the isolated fractions. The method of chemical analyses may include, but are not limited to, mass spectrometry, liquid-state and/or solid state proton or heteronuclear, one-dimensional or multi-dimensional nuclear magnetic resonance spectroscopy (NMR), ultraviolet spectroscopy, any of a variety of crystallographic methods, and any of a variety of other methods known in the art.

The safety and efficacy of the preferred compound of class of compounds effective in preventing hair loss and/or restoring hair growth may be established by any of a variety of standard such as animal models or human clinical trials. When choosing an appropriate model to determine efficacy of a method of composition or compound, or class of compound of the present invention, the skilled artisan will be capable of choosing an appropriate model, dose, and route of administration, and regime.

As will be appreciated by those of skill in the art, the preferred compound of class of compounds effective in preventing hair loss and/or restoring hair growth may be administered via a variety of methods, including but not limited to topical administration, as an injectable, or by oral, rectal or vaginal administration. The preferred method of administration is via topical administration directly the skin at the area effected, or likely to be effected by hair loss and/or hair thinning. Compositions for topical administration of for use as an injectable can be prepared in conventional forms, either as liquid solutions or suspensions, solid forms suitable for solution or suspension in liquid prior to injection, or as emulsions. Any of the known transdermal carriers can further be incorporated into topical formulations, such as DMSO or azone. Such transdermal carriers, and others, are known to facilitate delivery of topically-applied active ingredients across the stratum comeum (SC) and/or the stratum germinativum (SG). Accordingly, a topically applied composition having the hair loss preventing or hair growth restoring compound or class of compounds of the present invention may be a lotion, gel, or cream, using pharmaceutically-acceptable carriers, stabilizers, and excipients known to those of skill in the art.

Suitable excipients, whether used in topically-administered compositions or orally-administered compositions, are, for example, water, saline, dextrose, mannitol, lactose, lecithin, albumin, sodium glutamate, cysteine hydrochloride, and the like. In addition, if desired, the topical of injectable compositions may contain nontoxic auxiliary substances, such as wetting or buffering agents. In practicing the method of the invention, the compositions can be used alone or in combination with one another, or in combination with other therapeutic or diagnostic agents. For oral administration, the composition may be formulated and used as tablets, capsules or elixirs for oral administration; for rectal or vaginal administration, as a suppository; for other means of administration, be they as an injectable, parenterally, intravenously, subcutaneously, intramuscularly, colonically, nasally or intraperitoneally, the composition may be formulated as a sterile solution or suspension.

Furthermore, as will also be appreciated by those of skill in the art, the preferred compound of class of compounds effective in preventing hair loss and/or restoring hair growth may be chemically synthesized, rather than isolated from the root of a Vetiver grass, per se. Thus, while the preferred compound of class of compounds of the invention, effective in preventing hair loss and/or restoring hair growth, are isolatable from the root of a Vetriver grass, the compounds and class of compounds of the invention may be prepared, purified, and/or isolated in other manners. For example, to synthesize the preferred compound of class of compounds effective in preventing hair loss and/or restoring hair growth, one of skill in the art will typically first determine the chemical structure of the preferred compound of class of compounds. Any of a variety of synthetic methods may then be performed, using commercially-available starting materials, to generate the preferred compound or class of compounds in acceptable yields. Pharmaceutically carriers, excipients, stabilizers, preservatives and/or diluents may be added as deemed suitable by those of skill in the art.

The pharmaceutically effective amount of the composition required as a dose will depend on the route of administration, and the characteristics of the individual being treated. The dose can be tailored to achieve a desired effect by those of skill in the art; the does will typically depend on such factors as weight, diet, concurrent medication and other factors which those skilled in the art will recognize. Typically, doses having the concentration resulting from the aqueous extraction of, for example, Example 1, one tablespoon aliquots are applied topically from 1 to 42 times per week, including 5, 7, 12, 14, 18, 21, 24, 27, 28, 35, 38, and 40 times per week. Most preferably, one tablespoon aliquots are applied four times per day as follows: once approximately upon waking in the morning, once approximately at noon, once approximately at 6:00 p.m., and once approximately upon retiring in the evening.

As will be appreciated by those of skill in the art, the preferred compound or class of compounds effective in preventing hair loss and/or restoring hair growth may be administered topically as a lotion, gel, cream, or other salves or suspensions. Such lotions, gels, creams, or salves may preferably include agents suitable for cleansing the skin and/or hair in the affected, treated area.. Such agents include, but are not limited to, soaps, fatty acids, conditioners, and essential oils. Also, suitable thickeners, coloring agents, perfumes, aromatic agents, and/or preservatives may be added to the lotions, gels, creams, or other suspensions or salves as desired by the treated individual or the individual's companions. Such agents may be useful in disguising or enhancing the color and odor of the effective compound or class of compounds extracted or extractable from the Vetiver grass.

The composition of the present invention may be marketed. and/or used in conjunction with shampoos, conditions, styling gels, or other hair care products. For example, the composition of the present invention may be marketed and/or used in conjunction with a shampoo and/or a conditioner that improves the appearance or apparent thickness of hair. The present invention includes, but is not limited to, a method of cosmetic treatment. More specifically, the present invention includes the use of an extract of the root of a Vetiver grass in the treatment and/or the prevention of hair loss, and/or in the restoration or hair growth. The present invention also includes, but is not limited to, the use of an extract of the root of a Vetiver grass for the preparation of a medicament useful in the treatment and/or the prevention of hair loss, and/or in the restoration or hair growth. Preferably, the present invention encompasses the use of an extract of Vetiver grass for the preparation of a medicament for the treatment and/or the prevention of hair loss, and/or in the restoration or hair growth, in a male or female human. Most preferably, the present invention encompasses the use of an extract of the plant *Vetiveria zizanioides* (L.) Nash for the preparation of a medicament for the treatment and/or the prevention of the onset of *androgenetic alopecia*.

The present invention is described in detail through a variety of examples. It will be understood by those skilled in the art that the invention is not limited to the specific examples provided herein. Furthermore, although specific amounts of plant material and modes of extraction are specified in the following examples, it will be understood by those skilled in the art that the invention is not limited to these specific amounts and modes, and that variations in the amount of plant material, the mode or duration of extraction, and the method of administration, or more specifically, of application to the scalp and or skin, may be varied and still to achieve the desired effect of increasing the amount of hair growth and/or preventing hair loss or hair thinning.

EXAMPLE 1

PREPARATION OF AN AQUEOUS EXTRACT

Approximately 100 grams of the root of the plant *Vetiveria zizanioides* (L.) Nash was obtained and washed thoroughly under room temperature spring water. The root was allowed to dry for approximately one day at room temperature, and was not directly exposed to sunlight. The dried root was placed, fully submerged, into approximately 100 milliliters of purified water at room temperature. The mixture was let stand at room temperature for a period of not less than approximately 24 hours. The resultant water-based solution contained the aqueous extract.

EXAMPLE 2

TREATMENT OF HUMAN MALE WITH AN AQUEOUS EXTRACT

An individual human male, approximately 51 years of age, was identified as having experienced hair loss on his scalp, in a pattern typical of adult-onset, male-pattern baldness (androgenetic alopecia). The affected area had experienced no visible hair growth for at least 10 years, and this individual had not responded to treatment with Rogaine® (topical minoxidol) in the quantity and duration suggested by the manufacturer for a duration of twelve months. The extract, as prepared in Example 1, was applied topically to the affected areas of the individual's scalp in which hair loss was identified, in the following manner. Four times each day, approximately one tablespoon of this liquid was applied to the affected area, i.e., the crown and top of the scalp, and gently massaged into the skin. After such daily treatment for approximately three weeks, restored hair growth in the affected areas was detected.

At approximately three weeks from the first application, a peach-fuzz-like quantity of hair was detected. At approximately six weeks, more substantial growth and thickness of the individual's hair follicles was detected.

EXAMPLE 3

TREATMENT OF HUMAN MALE WITH AN AQUEOUS EXTRACT

An individual human male, approximately 54 years of age, was identified as beginning to experience and likely to experience further hair loss on his scalp, in a pattern typical of adult-onset, male-pattern baldness. Certain of this individual's genetic relatives, specifically, his brothers and maternal uncles, had experienced adult-onset, male-pattern baldness (*androgenetic alopecia*). An extract of the root of the plant *Vetiveria zizanioides* (L.) Nash was prepared substantially as described in Example 1. This extract was applied topically to the affected areas of the individual's scalp in which hair loss was identified, in the following manner. Each day, approximately two tablespoon of this liquid were applied to the affected area, i.e., the crown and top of the scalp, and gently massaged into the skin in two equal portions. Occasionally, the individual also applied the extract while washing and rinsing his hair in the typical manner. After such treatment for approximately one month, restored hair growth in the affected area was detected.

After approximately two years of continual use, the individual has experienced no additional hair loss, and the individual's hair has continued to appear thick.

EXAMPLE 4

TREATMENT OF HUMAN FEMALE WITH AN AQUEOUS EXTRACT

An individual human female, approximately 30 years of age, was identified as experiencing patches of hair loss and hair thinning on her scalp apparently due to the administration of an unrelated medication. The extract, as prepared in Example 1, was applied topically to the affected areas of the individual's scalp in which hair loss was identified, in the following manner. Four times each day, approximately one tablespoon of this liquid was applied to the affected areas and gently massaged into the skin.

After such daily treatment for approximately two weeks, restored hair growth in the affected areas was detected.

EXAMPLE 5

PREPARATION OF AND TREATMENT WITH AN AQUEOUS EXTRACT

Approximately 100 grams of the root of the plant *Vetiveria zizanioides* (L.) Nash is obtained and washed thoroughly under room temperature purified water. The root is allowed to dry for approximately one day at room temperature. The root is chopped into approximately 5 gram pieces, and those pieces are placed into approximately 100 milliliters of water that has been heated to a temperature of approximately 95° C. The root is placed in the boiling water and allowed to stand for not less than 24 hours.

An individual human male is identified as having been afflicted with adultonset, male pattern baldness. The liquid obtained from the above-described procedure is applied topically to the affected areas of the individual scalp as follows: Once each day, approximately one tablespoon of this liquid is applied to the affected areas, i.e., where hair loss or hair thinning is identified. This treatment continues from about three weeks to about nine weeks.

Restored hair growth and cessation of hair thinning are detected.

EXAMPLE 6

PREPARATION OF AND TREATMENT WITH AN ALCOHOLIC EXTRACT

Approximately 100 grams of the root of *Vetiveria zizanioides* is obtained and washed thoroughly under room temperature water. The root is allowed to dry for approximately one day at room temperature. The root is chopped into approximately twenty pieces of approximately equal weight, and those pieces are placed into a mixture of approximately 100 milliliters of water and approximately 100 ml of ethanol. This mixture is let stand at room temperature for a period of at least approximately one hour. The liquid is used to treat an individual human male identified as having experienced hair thinning as described in Example 2.

Cessation of hair thinning is observed after six weeks of treatment.

EXAMPLE 7

PREPARATION AND TREATMENT WITH AN ALCOHOLIC EXTRACT

Approximately 200 grams of the root of the *Vetiveria zizanioides* is obtained and washed thoroughly under room temperature water. The root is allowed to dry for approximately one day at room temperature. The root is pureed and placed into approximately 50 milliliters of isopropanol at room temperature. This mixture is let stand at room temperature for a period of approximately one day. The liquid is used to treat an individual human male with adult-onset male-pattern baldness as described in Example 3.

Cessation of hair thinning is observed after six weeks of treatment.

EXAMPLE 8

PREPARATION OF AND TREATMENT WITH A POLAR APROTIC EXTRACT

Approximately 400 grams of the root of the *Vetiveria zizanioides* is obtained and washed thoroughly under room temperature water. The root is allowed to dry for approximately one day at room temperature. The root is pureed and placed into approximately 20 milliliters of dimethylformamide (DMF). This mixture is let stand at room temperature for a period of approximately one day. The liquid is used to treat an individual human male with adult-onset male-pattern baldness (androgenetic alopecia) as described in Example 2.

Cessation of hair thinning is observed after six weeks of treatment.

EXAMPLE 9

PREPARATION OF AND TREATMENT WITH AN ORGANIC EXTRACT

Approximately 200 grams of the root of the *Vetiveria zizanioides* is obtained and washed thoroughly under room temperature water. The root is allowed to dry for approximately one day at room temperature. The root is pureed and placed into approximately 40 milliliters of benzene. This mixture is let stand at room temperature for a period of approximately one day. The liquid is used to treat an individual human male with adult-onset male-pattern baldness as described in Example 3.

Cessation of hair thinning is observed after six weeks of treatment.

What is claimed is:

1. A method for restoring hair growth comprising the steps of:
   identifying an individual suffering from or likely to suffer from hair loss; and
   administering an effective amount of an extract of the root of a Vetiver grass to the individual.

2. The method of claim 1, wherein the Vetiver grass comprises at least one subspecies of *Vetiveria zizanioides*.

3. The method of claim 1, wherein the Vetiver grass comprises *Vetiveria zizanioides* (L.) Nash.

4. The method of claim 1, wherein the extract is an aqueous extract.

5. The method of claim 1, wherein the extract is selected from the following: an alcoholic extract, a polar aprotic extract, and an organic extract other than an alcoholic extract or a polar aprotic extract.

6. The method of claim 1, wherein the individual is a human male.

7. The method of claim 1, wherein the extract is administered via topical administration to an area that has experienced or likely will experience hair loss.

8. The method of claim 7, wherein the area that has experienced or that likely will experience hair loss comprises a portion of the human scalp.

9. The method of claim 7, wherein the area has experienced hair loss.

10. The method of claim 1, wherein the extract is administered at least daily.

11. A method for preventing thinning hair comprising the steps of:
    identifying an individual suffering from or likely to suffer from thinning hair; and
    administering an effective amount of an extract of the root of a Vetiver grass to the individual.

12. The method of claim 11, wherein the Vetiver grass comprises at least one subspecies of *Vetiveria zizanioides*.

13. The method of claim 11, wherein the Vetiver grass comprises *Vetiveria zizanioides* (L.) Nash.

14. The method of claim 11, wherein the extract is an aqueous extract.

15. The method of claim 11, wherein the extract is selected from the following: an alcoholic extract, a polar aprotic extract, and an organic extract other than an alcoholic extract or a polar apotic extract.

16. The method of claim 11, wherein the individual is a human male.

17. The method of claim 11, wherein the extract is administered via topical administration to an area that has experienced or likely will experience hair thinning.

18. The method of claim 17, wherein the area that has experienced or that likely will experience hair thinning comprises a portion of the human scalp.

19. The method of claim 17, wherein the area has experienced hair thinning.

20. The method of claim 11, wherein the extract is administered at least daily.

* * * * *